US006666828B2

(12) United States Patent
Greco et al.

(10) Patent No.: US 6,666,828 B2
(45) Date of Patent: Dec. 23, 2003

(54) CATHETER SYSTEM HAVING DISPOSABLE BALLOON

(75) Inventors: Francesco Greco, Cantu (IT); Kenneth Jørgensen, Copenhagen (DK); Marianne Nielsen, Helsinge (DK); Anders Pedersen, Herlev (DK); Knud Aundal, Roskilde (DK)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/897,291

(22) Filed: Jun. 29, 2001

(65) Prior Publication Data

US 2003/0004434 A1 Jan. 2, 2003

(51) Int. Cl.[7] ................................. A61B 5/60
(52) U.S. Cl. ...................................... 600/561
(58) Field of Search ................. 600/561; 604/99.04, 604/103, 103.1; 606/194; 607/105

(56) References Cited

U.S. PATENT DOCUMENTS

| | | | |
|---|---|---|---|
| 4,023,562 A | | 5/1977 | Hynecek et al. |
| 4,191,196 A | | 3/1980 | Bradley et al. |
| 4,545,367 A | | 10/1985 | Tucci |
| 5,222,970 A | | 6/1993 | Reeves |
| 5,385,563 A | | 1/1995 | Gross |
| 5,391,178 A | | 2/1995 | Yapor |
| 5,449,345 A | | 9/1995 | Taylor et al. |
| 5,454,788 A | * | 10/1995 | Walker et al. ............ 604/99.04 |
| 5,549,554 A | | 8/1996 | Miraki |
| 5,766,081 A | | 6/1998 | Desmarais |
| 5,779,672 A | | 7/1998 | Dormandy, Jr. |
| 5,779,688 A | | 7/1998 | Imran et al. |
| 5,876,374 A | | 3/1999 | Alba et al. |
| 5,919,163 A | | 7/1999 | Glickman |
| 5,941,871 A | | 8/1999 | Adams et al. |
| 6,021,781 A | | 2/2000 | Thompson et al. |
| 6,136,258 A | | 10/2000 | Wang et al. |
| 6,139,570 A | * | 10/2000 | Saadat et al. ................ 607/105 |
| 6,231,524 B1 | | 5/2001 | Wallace et al. |

OTHER PUBLICATIONS

"Urethral Impedance Planimetry", Review from Medtronic's Sattelite Symposium, ICS Tampere, Finland.
"Urethral Pressure Measurement" to Gunnar Lose, Scand. J. Urol Nephrol. Supplement 207: 61–66, 2001.
"Neurology and Urodynamics" to Gunnar Lose, Official Journal of the Journal of the Urodynamics Society, vol. 11, No. 2, 1992.
"A System for Measurements of Micturition Urethral Cross–sectional Areas and Pressures" to Mortensen et al., Med. & Biol. Eng. & Comput., 1983, 21 482–488.
PCT International report, PTC, US 02/01542 (Jun. 24, 2002).

\* cited by examiner

*Primary Examiner*—Eric F. Winakur
*Assistant Examiner*—Brian Szmal
(74) *Attorney, Agent, or Firm*—Thomas F. Woods

(57) ABSTRACT

A disposable balloon catheter and corresponding catheter system are disclosed. In one embodiment, the catheter system comprises: (a) an elongated catheter comprising a first outer diameter, a first proximal end and a first distal end; (b) an elongated balloon carrier having a second proximal end, a second distal end and a second outer diameter, the second proximal end of the carrier and the first distal end of the catheter being configured to permit the first distal end of the catheter to matingly engage the second proximal end of the carrier, the second outer diameter of the balloon carrier being similar to the first outer diameter of the catheter; and (c) a disposable balloon formed from an expandable and resilient biocompatible material, the balloon having a lumen disposed between a third proximal end and a third distal end thereof, the lumen having at least a third inside diameter.

25 Claims, 5 Drawing Sheets

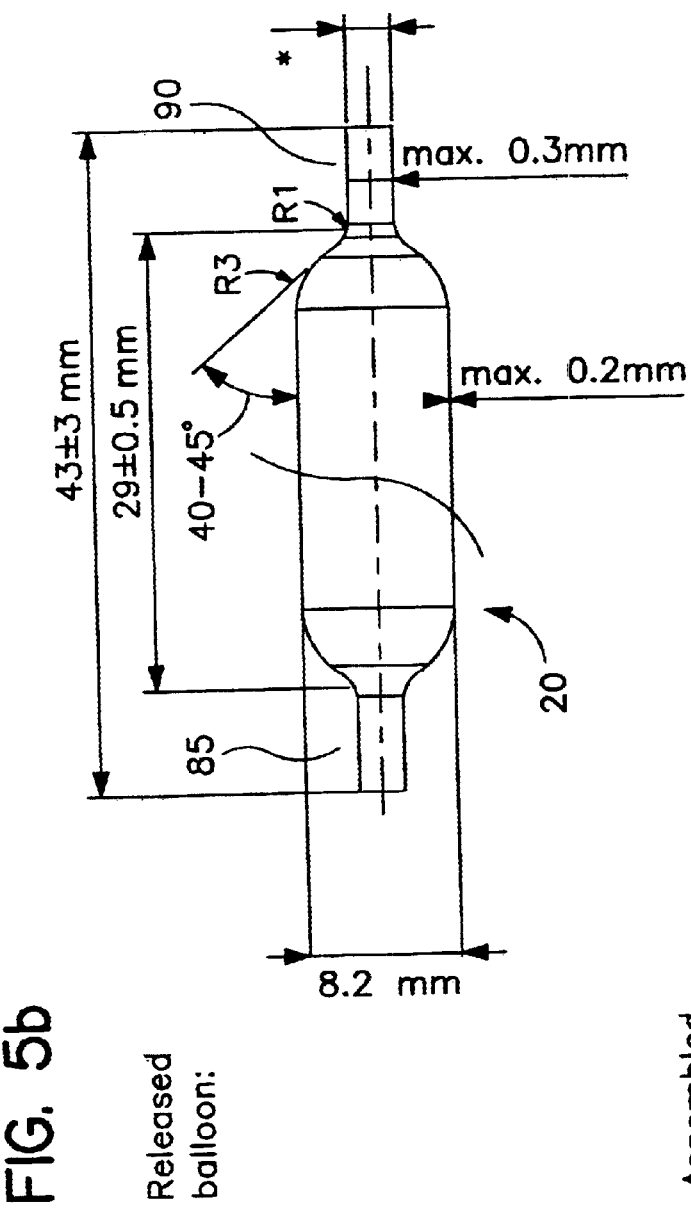
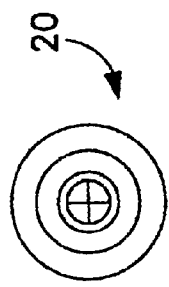
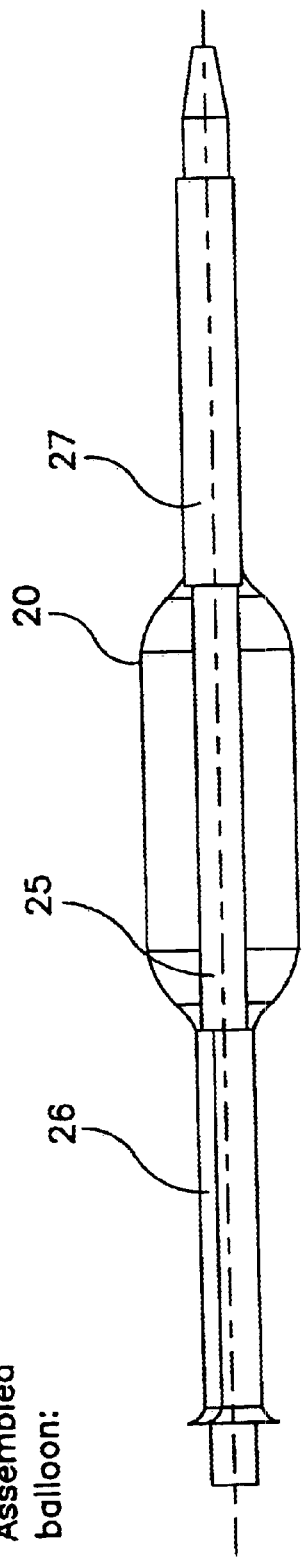

CATHETER SYSTEM HAVING DISPOSABLE BALLOON

FIELD OF THE INVENTION

This invention is generally directed to the field of medical catheter systems and balloons therefor.

BACKGROUND OF THE INVENTION

Urethral pressure measurements have been used for more than 75 years to assess urethral closure function. Urethral pressure and urethral closure pressure are idealized concepts which aim to represent the ability of the urethra to prevent leakage. So long as the intraurethral pressure exceeds the proximal fluid pressure, urine cannot leak and therefore the subject should be continent. Measurement of urethral pressures requires the introduction of a catheter adapted to perform such measurements. A variety of different techniques are employed to make urethral pressure measurements. Moreover, in the field of urethral impedance planimetry, it is known to measure the elasticity or "tonus" of the urethra, the cross-sectional area of the urethra, bladder pressure, abdominal pressure and detrusor pressure. EMGs and imaging data may also be obtained when making such measurements.

One well known technique for assessing a patient's bladder function is PCA (or "Pressure Cross-Sectional Area") catheter measurement as described, for example, in "A System for Measurement of Micturition Urethral Cross-Sectional Areas and Pressures" by Mortensen et al., Med. & Biol. Eng. & Comput., 1983, 21, 482–488; "Simultaneous Recording of Pressure and Cross-Sectional Area in the Female Urethra: A Study of Urethral Closure Function in Healthy and Stress Incontinent Women" by Lose in "Neurology and Urodynamics," Volume 11, Number 2, 1992; and "Urethral Pressure Measurement—Problems and Clinical Value" by Lose, Scand. J. Urol. Nephrol. Suppl. 207. See also "Urethral Impedance Planimetry" presented by Lose et al. at the Medtronic Satellite Symposium, ICS, Tampere, Finland, 2001.

FIG. 1 shows a prior art PCA catheter system 5 comprising catheter body 10, expandable and resilient balloon 20 mounted near distal end 30 of the catheter, balloon channel 40 for introducing saline solution 50 inside and removing saline solution 50 from balloon 20, distal micro-pressure transducer 60 mounted near distal tip 70 of catheter body 10, proximal micro-pressure transducer 65 mounted beneath a portion of balloon 20 and situated proximally from distal pressure transducer 60, and electrodes 80A, 80B, 80C and 80D mounted beneath balloon 20 on catheter body 10. Electrical connectors 9 at the proximal end of catheter system 5 permit electrical connections to be established between electrodes 80A through 80D, transducers 60 and 65, or temperature or other sensors, and external recording and/or analysis equipment (not shown in the Figures).

Cross-sectional area (or "A") is determined by delivering high frequency alternating current between excitation electrodes 80A and 80D and measuring the electrical conductivity of the saline solution inside balloon 20. Balloon 20 is then inflated and deflated incrementally with saline solution during rest and provocative maneuvers, and the drop in voltage between sensing electrodes 80B and 80D is measured. Using the field gradient principles described by Harris et al. in "Electrical Measurements of Urethral Flow" in "Urodynamics", New York, Academic Press, Chapter 34, page 465, cross-sectional area A may be determined. The pressure inside balloon 20 may be increased incrementally to induce dilation, and the resulting pressures may be recorded using the proximal and distal pressure transducers. The resulting pressure response curve is a stress relaxation curve, which may be analyzed to determine the elastic properties of the patient's urethra. Balloon 20 is preferably fully distensible within the physiological range of the urethral cross-sectional area.

It will now be seen that PCA catheter system 5 comprises several expensive components, most notably distal micro-pressure transducer 60, proximal micro-pressure transducer 65, and electrodes 80A, 80B, 80C and 80D. In addition, catheter system 5 requires the incorporation of balloon channel 40 and the inclusion and mounting of balloon 20. Because the cost of a single PCA catheter system 5 may easily exceed several thousand dollars, it is preferable that at least portions of PCA catheter system 5 be reusable following sterilization.

To date, some PCA catheters have been re-used by mounting disposable balloons on catheter body 10 using sutures or ties 75 that are secured around the proximal and distal ends 85 and 90 of balloon 20. Mounting balloon 20 on catheter body 10 using such manual attachment techniques is time consuming, tedious and does not produce reliable seals between proximal and distal ends 85 and 90 of balloon 29 and the outside diameter of the catheter. What is needed is a PCA catheter system having a disposable balloon which may be readily and quickly mounted on or removed from a catheter body, and which also provides a competent non-leaking seal between the balloon and the catheter when the balloon is filled with saline solution.

Patents and printed publications describing various aspects of the foregoing and other problems, as well as the state of the art, are listed below.

1. U.S. Pat. No. 4,023,562 to Hynecek et al. entitled "Miniature Pressure Transducer for Medical Use and Assembly Method."

2. U.S. Pat. No. 4,191,196 to Bradley et al. entitled "Profilometry Method and Apparatus" to Ellis.

3. U.S. Pat. No. 4,545,367 to Tucci entitled "Detachable Balloon Catheter and Method of Use."

4. U.S. Pat. No. 5,385,563 to Gross entitled "Urodynamic Catheter."

5. U.S. Pat. No. 5,449,345 to Taylor et al. entitled "Detachable and Reusable Digital Control Unit for Monitoring Balloon Catheter Data in a Syringe Inflation System."

6. U.S. Pat. No. 5,549,554 to Miraki entitled "Catheters Having Separable Reusable Components."

7. U.S. Pat. No. 5,766,081 to Kreder entitled "Urethral Pressure Catheter."

8. U.S. Pat. No. 5,779,688 to Imran et al. entitled "Low Profile Balloon-On-A-Wire Catheter with Shapeable And/Or Deflectable Tip and Method."

9. U.S. Pat. No. 5,876,374 to Alba et al. entitled "Catheter Sleeve for Use with a Balloon Catheter."

10. U.S. Pat. No. 5,919,163 to Glickman entitled "Catheter with Slideable Balloon."

11. U.S. Pat. No. 5,941,871 to Adams et al. entitled "Catheter Systems with Interchangeable Parts."

12. U.S. Pat. No. 6,021,781 to Thompson et al. entitled "Intraurethral Pressure Monitoring Assembly and Method of Treating Incontinence Using Same."

13. U.S. Pat. No. 6,136,258 to Wang et al. entitled "Method of Forming a Co-Extruded Balloon for Medical Purposes."

14. U.S. Pat. No. 6,231,524 to Wallace et al. entitled "Pressure Device with Enhanced Fluid Monitoring Features."

All patents and printed publications listed hereinabove are hereby incorporated by reference herein, each in its respective entirety. As those of ordinary skill in the art will appreciate readily upon reviewing the drawings set forth herein and upon reading the Summary of the Invention, Detailed Description of the Preferred Embodiments and Claims set forth below, at least some of the devices and methods disclosed in the patents and publications listed hereinabove may be modified advantageously in accordance with the teachings of the present invention.

SUMMARY OF THE INVENTION

Various embodiments of the present invention have certain objects. That is, various embodiments of the present invention provide solutions to problems existing in the prior art, including, but not limited to, one or more of the problems listed above.

Various embodiments of the present invention have certain advantages, including, without limitation, one or more of: (a) permitting expensive catheter components or catheters to be re-used; (b) reducing the amount of time required to mount a disposable balloon on a catheter; (c) reducing the cost of medical procedures carried out using the balloon of the present invention; (d) increasing the competence and leakworthiness of seals made using the balloon of the present invention; (e) obtaining more reliable and accurate data; (e) providing disposable balloons at reduced cost; and (f) providing balloons having improved mechanical characteristics such as increased tensile strength, increased elasticity and improved resistance to rupture or tear.

Various embodiments of the present invention have certain features, including one or more of the following: (a) a slideable balloon; (b) a balloon carrier configured to engage a catheter and permit a balloon disposed thereon to be slideably moved from the carrier to the catheter; (c) a balloon having proximal and distal ends which slideably engage and seal around a corresponding balloon carrier or catheter; (d) a balloon configured to sealingly engage the outside diameter of a catheter body and prevent saline solution disposed therewithin from leaking therewithout; (e) a disposable balloon formed from an expandable and resilient biocompatible material; (f) a PCA catheter comprising at least one of a plurality of pressure transducers, a plurality of impedance measurement electrodes, and a means for delivering high frequency alternating current between excitation electrodes; and (g) proximal and distal removable sleeves disposed between the inside diameter of the proximal and distal ends of the balloon and the outer diameter of the carrier or catheter.

In one embodiment of the present invention, a catheter system is provided having a disposable balloon, where the system comprises an elongated catheter comprising a first outer diameter, a first proximal end and a first distal end; an elongated balloon carrier having a second proximal end, a second distal end and a second outer diameter, the second proximal end of the carrier and the first distal end of the catheter being configured to permit the first distal end of the catheter to matingly or otherwise suitably engage the second proximal end of the carrier, the second outer diameter of the balloon carrier being similar to the first outer diameter of the catheter, and a disposable balloon formed from an expandable and resilient biocompatible material, the balloon having a lumen disposed between a third proximal end and a third distal end thereof, the lumen having at least a third inside diameter, the second diameter of the carrier and the third diameter of the balloon being configured to permit the balloon first to be slideably mounted onto the balloon carrier and second to be slideably moved from the carrier onto the catheter when the second proximal end of the carrier is matingly or otherwise suitably engaged with the first distal end of the catheter.

In another embodiment of the present invention, a disposable balloon for use in a catheter system is provided, where the system comprises an elongated catheter having a first outer diameter, a first proximal end and a first distal end, an elongated balloon carrier having a second proximal end, a second distal end and a second outer diameter, the second proximal end of the carrier and the first distal end of the catheter being configured to permit the first distal end of the catheter to matingly or otherwise suitably engage the second proximal end of the carrier, the second outer diameter of the balloon carrier being similar to the first outer diameter of the catheter, the balloon being formed from an expandable and resilient biocompatible material, and where the balloon comprises a lumen disposed between a third proximal end and a third distal end thereof, and at least a third inside diameter, wherein the second diameter of the carrier and the third diameter of the balloon are configured to permit the balloon first to be slideably mounted onto the balloon carrier and second to be slideably moved from the carrier onto the catheter when the second proximal end of the carrier is matingly or otherwise suitably engaged with the first distal end of the catheter.

In another embodiment of the present invention, there is provided a method of making a disposable balloon for use in a catheter system comprising an elongated catheter having a first outer diameter, a first proximal end and a first distal end, an elongated balloon carrier having a second proximal end, a second distal end and a second outer diameter, the second proximal end of the carrier and the first distal end of the catheter being configured to permit the first distal end of the catheter to matingly or otherwise suitably engage the second proximal end of the carrier, the second outer diameter of the balloon carrier being similar to the first outer diameter of the catheter, the balloon being formed from an expandable and resilient biocompatible material, the method comprising providing a mandrel having an outside surface defining a desired internal shape of the balloon; providing a container having a biocompatible liquid silicone disposed therein; dipping the mandrel in the liquid silicone to form a coated mandrel; removing the coated mandrel from the liquid silicone;
heating the coated mandrel in an oven to form a heat cured balloon; removing the mandrel and heat cured balloon from the oven, and removing the heat cured balloon from the mandrel.

Methods of mounting a disposable balloon on a catheter using a carrier are also provided.

BRIEF DESCRIPTION OF THE DRAWINGS

The present invention will become better understood by reference to the following Detailed Description of the Preferred Embodiments of the present invention when considered in connection with the accompanying Figures, in which like numbers designate like parts throughout, and where:

FIG. 5a shows a side view of one embodiment of a disposable balloon and carrier of the present invention;

FIG. 5b shows in detail some representative aspects and features of the balloon of FIG. 5a; and FIG. 5c shows an end cross-sectional view of the balloon of FIGS. 5a and 5b.

DETAILED DESCRIPTION OF THE PREFERRED EMBODIMENTS

Figure 2:
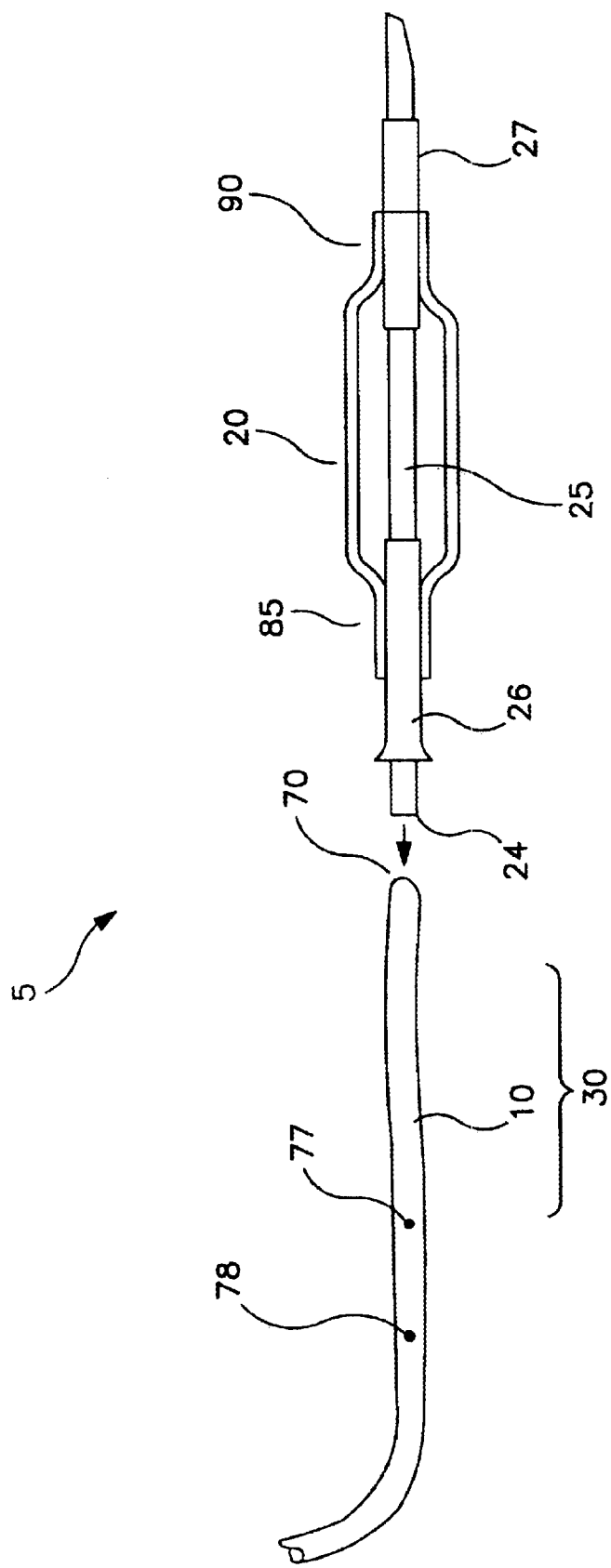
FIG. 2 shows a simplified cross-sectional view of one embodiment of a catheter system of the present invention prior to a disposable balloon being mounted on a PCA catheter.

FIG. 2 shows a simplified cross-sectional view of one embodiment of catheter system 5 of the present invention prior to disposable balloon 20 being mounted on a PCA catheter having catheter body 10. Balloon 20 is slideably mounted on carrier 25 such that optional proximal and distal disposable sleeves 26 and 27 are located between the inner diameters of the proximal and distal ends of balloon 20 and the outer diameter of carrier 25. Proximal end 24 of carrier 25 is adapted to matingly or otherwise suitably engage distal tip 70 of catheter body 10. Accordingly, tip 70 and end 24 most preferably have correspondingly complementary geometric shapes. Carrier 25 and sleeves 26 and 27 are most preferably formed of medical grade polyethylene although other materials well known in the art may also be used. Holes 77 and 78 permit fluid to be delivered into or removed from balloon 20. Pressure transducers are not shown in FIGS. 2 through 5c, although are employed in a preferred embodiment of the present invention.

Figure 3:
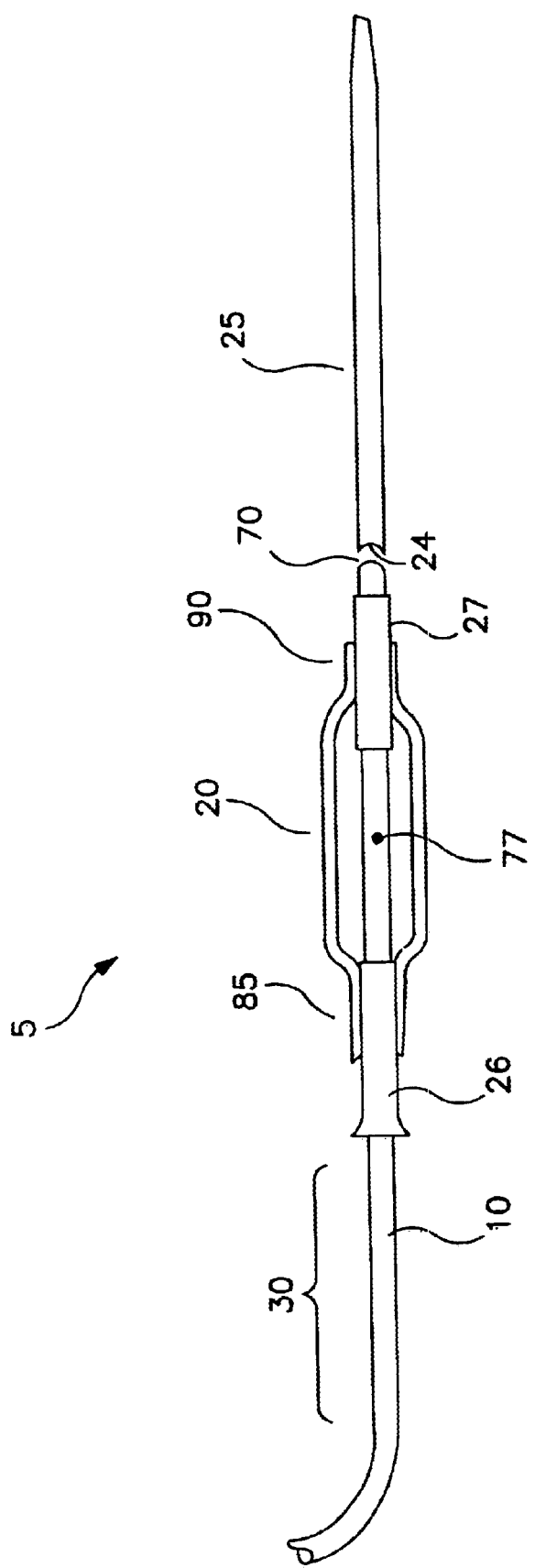
FIG. 3 shows a simplified cross-sectional view of the catheter system of FIG. 2 after the disposable balloon has been mounted on the distal end of the PCA catheter.
Figure 4:
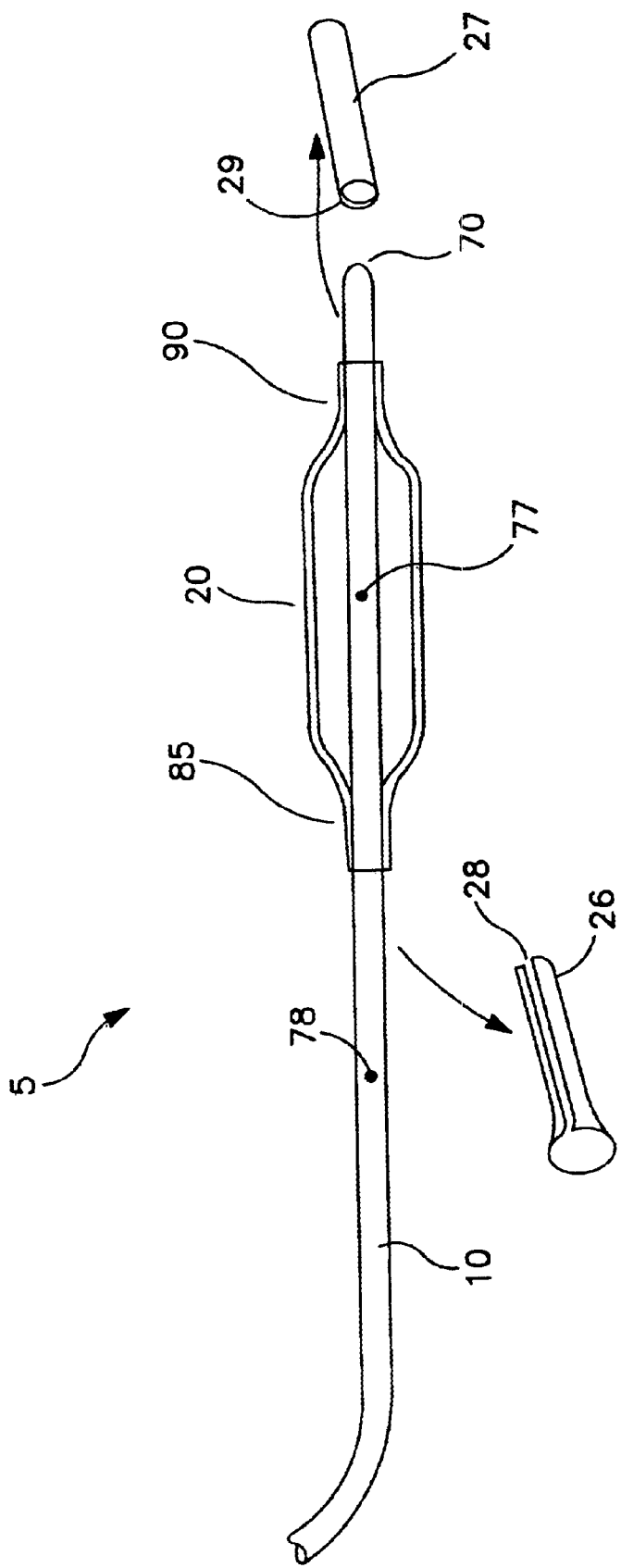
FIG. 4 shows a simplified cross-sectional view of the catheter system of FIG. 3 after the proximal and distal disposable sleeves have been removed from underneath the proximal and distal ends of the balloon.

FIG. 3 shows a simplified cross-sectional view of the catheter system of FIG. 2 after the disposable balloon has been mounted on distal end 30 of catheter 10. Sleeves 26 and 27 are gripped by a physician and the balloon and sleeves are pushed in a proximal direction so that the sleeves and balloon move onto catheter body 10 and off of carrier 25. Once balloon 20 has been positioned in an appropriate location along catheter body 10, and as shown in FIG. 4, proximal and distal disposable sleeves 26 and 27 are removed from underneath proximal and distal ends 85 and 90 of balloon 20. Sleeves 26 and 27 preferably include cuts 28 and 29 so that sleeves 26 and 27 may be readily and easily removed from around catheter body 10.

FIG. 5a shows a side view of one embodiment of disposable balloon 10 and carrier 25 of the present invention. FIG. 5b shows in detail some representative aspects, features and measurements of balloon 20 of FIG. 5a. FIG. 5c shows an end cross-sectional view of balloon 20 of FIGS. 5a and 5b.

Figure 1:
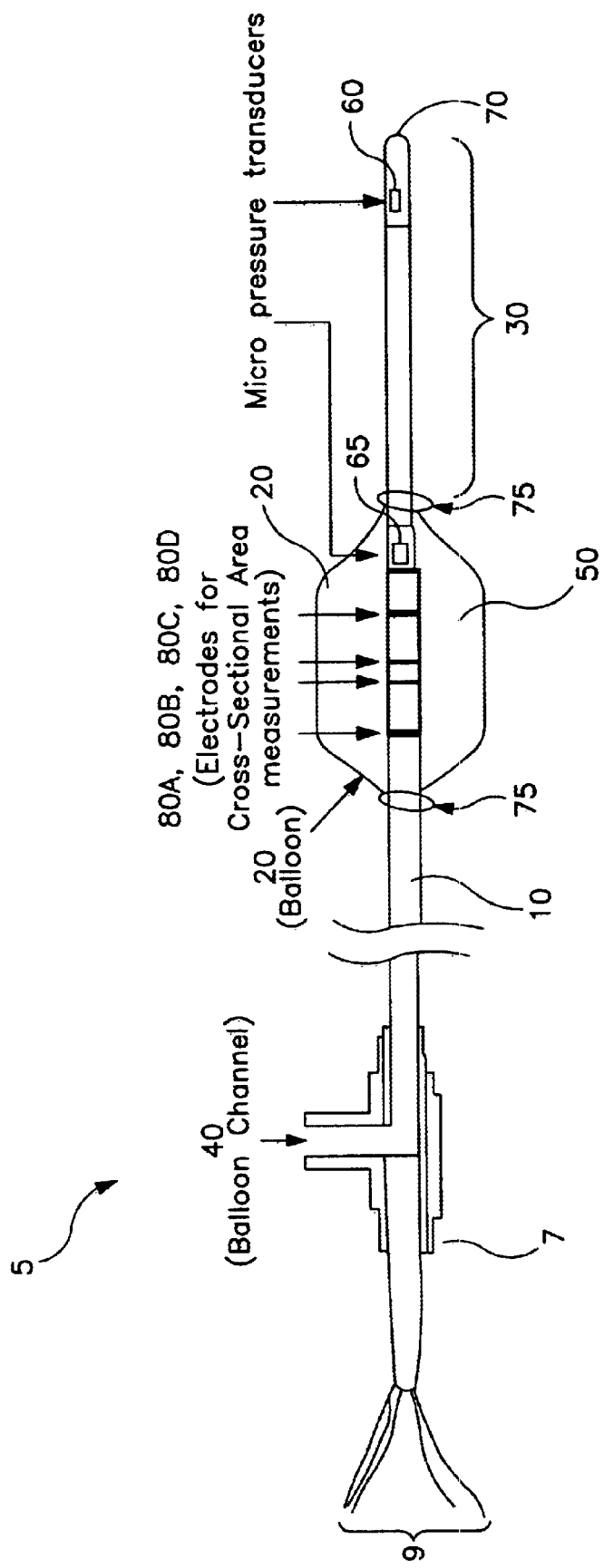
FIG. 1 shows a simplified cross-sectional view of a prior art PCA catheter.

Catheter system 5 may comprise a PCA or other type of catheter, and may or may not include balloon channel 40. Catheter system 5 of the present invention may or may not include electrodes 80A, 80B, 80C or 80D, as shown in FIG. 1, and may or may not include other transducers such as one or more temperature sensors. In a preferred PCA catheter embodiment of the present invention, a plurality of pressure transducers is mounted on the catheter and comprises a first pressure transducer mounted at or near the first distal end of the catheter and a second pressure transducer mounted on the catheter at a location proximal from the first pressure transducer. A preferred PCA catheter of the present invention also comprises a plurality of inner impedance measurement or sensing electrodes and a plurality of outer excitation electrodes, the electrodes being mounted on the catheter at or between the first distal end and the first proximal end thereof, and means for delivering high frequency alternating current between the excitation electrodes. Additionally, a preferred PCA catheter of the present invention includes means 40 for introducing fluid into and withdrawing fluid from balloon 20.

In the present invention, it is preferred that a third inside diameter of the lumen of balloon 20 tightly engage a second outside diameter of carrier 25 near or at the proximal and distal ends 85 and 90 of balloon 20 so as to prevent leakage. That is, the balloon material, the third diameter of the balloon and the first diameter of the catheter are preferably configured to sealingly engage the third inside diameters of the proximal and distal ends of the balloon against the first outside diameter of the balloon so as to prevent a fluid introduced inside the balloon from leaking outside the balloon.

Preferred lengths of balloon 20 of the present invention may range between about 5 mm and about 100 mm, between about 10 mm and about 80 mm, between about 20 mm and about 60 mm, between about 35 mm and about 55 mm, and between about 40 mm and about 50 mm. The preferred wall thickness of balloon 20 of the present invention may range between about 0.05 mm and about 1 mm, between about 0.1 mm and about 0.5 mm, between about 0.15 mm and about 0.35 mm, and between about 0.2 mm and about 0.3 mm. In a preferred embodiment of the present invention, the aforementioned third diameter may range between about 3 mm and about 15 mm, about 4 mm and about 12 mm, about 5 mm and about 10 mm, and about 6 mm and about 9 mm. It is also preferred that the balloon lumen comprise a fourth inside diameter that is greater than the third inside diameter, where at least portions of the lumen are disposed near or at the third proximal end and the third distal end has the third inside diameter, and where at least portions of the lumen are disposed between the third proximal end and the third distal end has the fourth inside diameter. The fourth diameter preferably ranges between about 2 mm and about 20 mm, about 4 mm and about 15 mm, and between about 6 mm and about 10 mm.

The balloon preferably comprises medical grade silicone having a tensile strength ranging between about 200 psi and about 3000 psi, or between about 1000 psi and about 2000 psi, and has a Shore durometer hardness ranging between about 5 ShA and about 100 ShA or between about 30 ShA and about 70 ShA. The materials from which balloon 20 is formed preferably meets or exceeds USP Class IV, ASTM-D412, 471 and 4754, and ISO 10993-3, 4, 5, 6, 10 and 11 standards. The material employed to form balloon 20 should also pass suitable tests for cytotoxicity, sensitization, irritation, systemic toxicity, hemocompatibility, and hemolysis. One such preferred medical grade silicone material may be obtained from NUSIL SILICONE TECHNOLOGY.

A preferred method of making the disposable balloon of the present invention is to mix a suitable two-part liquid silicone formulation obtained from NUSIL SILICONE TECHNOLOGY in a vat at room temperature, provide a stainless steel mandrel having an outside surface defining a desired internal shape of the balloon, provide a container having a biocompatible liquid silicone disposed therein, dip the mandrel in the liquid silicone to form a coated mandrel, remove the coated mandrel from the liquid silicone, heat the coated mandrel in an oven at about 130 degrees Centigrade for about half an hour to form a heat cured balloon, remove the mandrel and heat cured balloon from the oven, and remove the heat cured balloon from the mandrel.

Although specific embodiments of the invention are described here in some detail, it is to be understood that those specific embodiments are presented for the purpose of illustration, and are not to be taken as somehow limiting the scope of the invention defined in the appended claims to those specific embodiments. It is also to be understood that various alterations, substitutions, and modifications may be made to the particular embodiments of the present invention described herein without departing from the spirit and scope of the appended claims. It is further to be understood that the scope of the disposable balloon and carrier system of the present invention is not limited to PCA catheters and systems, but extends to esophageal, rectal, gastrointestinal, intestinal and other devices and systems where it is desirable to have a disposable balloon in combination with a reusable catheter and associated sensors and/or fluid or drug delivery system.

In the claims, means plus function clauses are intended to cover the structures and devices described herein as performing the recited function and their equivalents. Means plus function clauses in the claims are not intended to be limited to structural equivalents only, but are also intended to include structures and devices which function equivalently in the environment of the claimed combination.

All printed publications, patents and patent applications referenced hereinabove are hereby incorporated by referenced herein, each in its respective entirety.

We claim:

1. A catheter system having a disposable balloon, comprising:
   (a) an elongated PCA catheter comprising a first outer diameter, a first proximal end and a first distal end;
   (b) an elongated balloon carrier having a second proximal end, a second distal end and a second outer diameter, the second proximal end of the carrier and the first distal end of the PCA catheter being configured to permit the first distal end of the PCA catheter to matingly engage the second proximal end of the carrier, the second outer diameter of the balloon carrier being similar to the first outer diameter of the PCA catheter; and
   (c) a disposable balloon formed from an expandable and resilient biocompatible material, the balloon having a lumen disposed between a third proximal end and a third distal end thereof, the lumen having at least a third inside diameter, the second diameter of the carrier and the third diameter of the balloon being configured to permit the balloon first to be slideably mounted onto the balloon carrier and second to be slideably moved from the carrier onto the PCA catheter when the second proximal end of the carrier is matingly engaged with the first distal end of the PCA catheter.

2. The catheter system of claim 1, wherein a plurality of pressure transducers are mounted on the catheter at or between the first distal end and the first proximal end thereof.

3. The catheter system of claim 2, wherein the plurality of pressure transducers comprises a first pressure transducer mounted at or near the first distal end of the catheter and a second pressure transducer mounted on the catheter at a location proximal from the first pressure transducer.

4. The catheter system of claim 1, wherein the catheter further comprises a plurality of impedance measurement electrodes, the electrodes being mounted on the catheter at or between the first distal end and the first proximal end thereof.

5. The catheter system of claim 4, wherein the plurality of impedance measurement electrodes comprises two anodal ring electrodes and two cathodal ring electrodes.

6. The catheter system of claim 4, further comprising means for delivering high frequency alternating current between the electrodes.

7. The catheter system of claim 1, wherein the third inside diameter of the lumen engages the second outside diameter of the carrier near or at the proximal and distal ends of the balloon.

8. The catheter system of claim 7, wherein proximal and distal removable sleeves are disposed, respectively, between the third inside diameter of the proximal and distal ends of the lumen and the second outer diameter of the carrier.

9. The catheter system of claim 1, wherein the length between the proximal and distal ends of the balloon is selected from the group consisting of ranging between about 5 mm and about 100 mm, ranging between about 10 mm and about 80 mm, ranging between about 20 mm and about 60 mm, ranging between about 35 mm and about 55 mm, and ranging between about 40 mm and about 50 mm.

10. The catheter system of claim 1, wherein the balloon has a wall thickness selected from the group consisting of ranging between about 0.05 mm and about 1 mm, ranging between about 0.1 mm and about 0.5 mm, ranging between about 0.15 mm and about 0.35 mm, and ranging between about 0.2 mm and about 0.3 mm.

11. The catheter system of claim 1, wherein the third diameter is selected from the group consisting of ranging between about 3 mm and about 15 mm, ranging between about 4 mm and about 12 mm, ranging between about 5 mm and about 10 mm, and ranging between about 6 mm and about 9 mm.

12. The catheter system of claim 1, wherein the lumen further comprises a fourth inside diameter that is greater than the third inside diameter, at least portions of the lumen disposed near or at the third proximal end and the third distal end having the third inside diameter, at least portions of the lumen disposed between the third proximal end and the third distal end having the fourth inside diameter.

13. The catheter system of claim 1, wherein the fourth inside diameter is selected from the group consisting of between about 2 mm and about 20 mm, ranging between about 4 mm and about 15 mm, and ranging between about 6 mm and about 10 mm.

14. The catheter system of claim 1, wherein the catheter is a PCA catheter comprising means for introducing fluid into and withdrawing fluid from the balloon.

15. The catheter system of claim 1, wherein the balloon material, the third diameter of the catheter and the first diameter of the catheter are configured to sealingly engage the third inside diameters of the proximal and distal ends of the balloon against the first outside diameter of the catheter so as to prevent a fluid introduced inside the balloon from leaking outside the balloon.

16. The catheter system of claim 1, wherein the balloon comprises medical grade silicone.

17. The catheter system of claim 1, wherein the balloon comprises a material having a tensile strength selected from the group consisting of ranging between about 200 psi and about 3000 psi, and ranging between about 1000 psi and about 2000 psi.

18. The catheter system of claim 1, wherein the balloon comprises a material having a Shore durometer hardness selected from the group consisting of ranging between about 5 ShA and about 100 ShA, and ranging between about 30 ShA and about 70 ShA.

19. A catheter system having a disposable balloon, comprising:
(a) an elongated catheter comprising a first outer diameter, a first proximal end and a first distal end;
(b) an elongated balloon carrier having a second proximal end, a second distal end and a second outer diameter, the second proximal end of the carrier and the first distal end of the catheter being configured to permit the first distal end of the catheter to matingly engage the second proximal end of the carrier, the second outer diameter of the balloon carrier being similar to the first outer diameter of the catheter; and
(c) a disposable balloon formed from an expandable and resilient biocompatible material, the balloon having a lumen disposed between a third proximal end and a third distal end thereof, the lumen having at least a third inside diameter that engages the second outside diameter of the carrier near or at the proximal and distal ends of the balloon, the second diameter of the carrier and the third diameter of the balloon being configured to permit the balloon first to be slideably mounted onto the balloon carrier and second to be slideably moved from the carrier onto the catheter when the second proximal end of the carrier is matingly engaged with the first distal end of the catheter,
wherein proximal and distal removable sleeves are disposed, respectively, between the third inside diameter of the proximal and distal ends of the lumen and the second outer diameter of the carrier.

20. The catheter system as in claim 19 wherein the catheter is selected from the group consisting of an esophageal catheter, a rectal catheter, a gastrointestinal catheter, and an intestinal catheter.

21. The catheter system of claim 19, wherein a plurality of pressure transducers are mounted on the catheter at or between the first distal end and the first proximal end thereof.

22. The catheter system of claim 21, wherein the plurality of pressure transducers comprises a first pressure transducer mounted at or near the first distal end of the catheter and a second pressure transducer mounted on the catheter at a location proximal from the first pressure transducer.

23. The catheter system of claim 19, wherein the catheter further comprises a plurality of impedance measurement electrodes, the electrodes being mounted on the catheter at or between the first distal end and the first proximal end thereof.

24. The catheter system of claim 23, wherein the plurality of impedance measurement electrodes comprises two anodal ring electrodes and two cathodal ring electrodes.

25. The catheter system of claim 23, further comprising means for delivering high frequency alternating current between the electrodes.

* * * * *